(12) United States Patent
Sisson

(10) Patent No.: US 12,336,762 B2
(45) Date of Patent: Jun. 24, 2025

(54) COLOR CHECKER DEVICE FOR A FUNDUS IMAGING CAMERA

(71) Applicant: Christye P. Sisson, Pittsford, NY (US)

(72) Inventor: Christye P. Sisson, Pittsford, NY (US)

(73) Assignee: Rochester Institute of Technology, Rochester, NY (US)

( * ) Notice: Subject to any disclaimer, the term of this patent is extended or adjusted under 35 U.S.C. 154(b) by 542 days.

(21) Appl. No.: 17/661,092

(22) Filed: Apr. 28, 2022

(65) Prior Publication Data

US 2022/0346644 A1 Nov. 3, 2022

Related U.S. Application Data

(60) Provisional application No. 63/180,885, filed on Apr. 28, 2021.

(51) Int. Cl.
| | |
|---|---|
| *A61B 3/14* | (2006.01) |
| *A61B 3/12* | (2006.01) |
| *G06T 7/80* | (2017.01) |
| *G06T 7/90* | (2017.01) |

(52) U.S. Cl.
CPC ............ *A61B 3/14* (2013.01); *A61B 3/12* (2013.01); *G06T 7/80* (2017.01); *G06T 7/90* (2017.01); *A61B 2560/0233* (2013.01); *G06T 2207/10024* (2013.01); *G06T 2207/30201* (2013.01)

(58) Field of Classification Search
CPC ..... A61B 3/14; A61B 3/12; A61B 2560/0233; G06T 7/80; G06T 7/90; G06T 2207/10024; G06T 2207/30201
USPC .......................................................... 351/206
See application file for complete search history.

(56) References Cited

U.S. PATENT DOCUMENTS

| | | | |
|---|---|---|---|
| 6,595,643 B2 * | 7/2003 | Levine .................. | A61F 9/008 351/221 |
| 2002/0047988 A1 | 8/2002 | Matsumoto | |
| 2003/0007154 A1 * | 1/2003 | Tandon .................. | G01J 3/513 356/406 |
| 2003/0063302 A1 * | 4/2003 | Munger ............. | B41F 33/0036 358/1.9 |
| 2008/0204829 A1 * | 8/2008 | Harrington .......... | H04N 1/6094 358/504 |

(Continued)

OTHER PUBLICATIONS

Jansen et al., "Learning Curve Evaluation Upskilling Retinal Imaging Using Smartphones," Scientific Reports, 11:12691 (2021).

(Continued)

*Primary Examiner* — Mohammed A Hasan
(74) *Attorney, Agent, or Firm* — Bond, Schoeneck & King, PLLC; Joseph M. Noto

(57) ABSTRACT

A color checker device is disclosed. The color checker device includes a substrate configured to be inserted into a model eye and to conform to a surface curvature of the model eye when inserted therein. A color test target is located on the substrate. The color test target comprises a plurality of color sections configured for generating a color characterization profile of a fundus imaging camera configured to capture a color image of a human retina. A method of generating a color characterization profile using the color checker device and a fundus imaging system having the color characterization profile stored thereon are also disclosed.

19 Claims, 11 Drawing Sheets
(8 of 11 Drawing Sheet(s) Filed in Color)

(56) References Cited

U.S. PATENT DOCUMENTS

2013/0003016 A1 1/2013 Feldon et al.
2016/0360167 A1* 12/2016 Mitchell .............. H04N 9/3182

OTHER PUBLICATIONS

Kim et al., "Comparison of Smartphone Ophthalmoscopy vs Conventional Direct Ophthalmoscopy as a Teaching Tool for Medical Students: The COSMOS Study," Clinical Ophthalmology 13:391-401 (2019).

Ramsden, "Ophthalmology Imaging: The Importance of Color Reproduction," Tech Briefs, Imaging, (2013).

Bull, "Color Management for Ophthalmic Fundus Photography," The Journal of Ophthalmic Photography, 31(1),:40-44 (2009).

Bennett, "Maximizing Quality in Ophthalmic Digital Imaging," The Journal of Ophthalmic Photography, 31(1):32-39 (2011).

Fischer et al., Photographic Reading Center of the Idiopathic Intracranial Hypertension Treatment Trial (IIHTT): Methods and Baseline Results, 56(5):3292-303 (2015).

Hubbard et al., "Brightness, Contrast, and Color Balance of Digital versus Film Retinal Images in the Age-Related Eye Disease Study 2," Investigative Ophthalmology & Visual Science, 49(8):3268-82 (2008).

Bae et al., "Why Some Colors Appear More Memorable Than Others: A Model Combining Categories and Particulars in Color Working Memory," Journal of Experimental Psychology 144 (4):744-63 (2015).

Im et al., "A Deep Learning Algorithm to Detect Chronic Kidney Disease From Retinal Photographs in Community-Based Populations," Lancet Digital Health, 2:e295-302 (2020).

Sisson et al., "Analysis of Color Consistency in Retinal Fundus Photography: Application of Color Management and Development of an Eye Model Standard," Analytical Cellular Pathology, 1-2 (2014).

Badano et al., "Consistency and Standardization of Color in Medical Imaging: A Consensus Report," J Digit Imaging, 28:41-52 (2015).

\* cited by examiner

FIG. 12B (cont.)

COLOR CHECKER DEVICE FOR A FUNDUS IMAGING CAMERA

CROSS REFERENCE

This application claims the benefit of the filing date of U.S. Provisional Patent Application No. 63/180,885, filed Apr. 28, 2021, which is hereby incorporated by reference in its entirety.

FIELD

The present disclosure relates to a color checker device for a fundus imaging camera. More specifically, the present disclosure relates to a color checker device configured for generating a color characterization profile of a fundus imaging camera configured to capture a color image of a human retina, a method of generating a color characterization profile using the color checker device, and a fundus imaging system having a color characterization profile generated using the color checker device stored thereon.

BACKGROUND

The field of fundus imaging originated with film photography. Film-based mydriatic fundus cameras gained wide use in ophthalmology in the early 1970's, giving rise to fundus photographs acting as patient records for what a patient's retina looked like on that visit. This technology was extended to include a dye-test (fluorescein angiogram), which was injected into the body and photographed using black and white film at the time, making ophthalmic photography the only type of photography that was diagnostic in that it provided information the physician could not otherwise see.

When digital sensors began to replace color slide films in the 1990's, the field of ophthalmic photography evolved from viewing a developed roll of film/color slide or print to a digital image that was displayed instantly on a screen. Up until this point, the color of the retinal image was one that was determined entirely by the manufacturer of the film (Kodak, or to a much lesser extent, Fuji) through the chemical processes that were used to develop that film into a color slide image.

While the transition to digital afforded quite a few advantages, it was now the responsibility of the fundus camera manufacturers to figure out what these retinal images should look like, and how to control that look, which included adjusting the color response and the contrast. In the early 90's, the field of digital color management in photography was not yet fully formed, so many manufacturers would install the fundus imaging systems, take a photograph of an object with the camera (a dollar bill, alcohol wipe etc.) and adjust the camera's color according to what they thought it should be, usually by changing the way the camera actually saw color (accessing a INI or initialization file extension). On some occasions, if a customer/physician complained about the image, the technician would then adjust those color settings until the ophthalmologist was satisfied with the retinal images they were getting.

It is worth noting that the color reference for human retinas up until this point was from two sources; one being the in-person examination of the retina using an indirect ophthalmoscope by the ophthalmologist (often using a halogen bulb and a handheld lens) and the other being slide film, most commonly Kodachrome or Ektachrome. These physicians, as well as generations of doctors since then, have held up these film-based images as gold standards of retinal imaging, because they were the basis (and literally, the image standards) for studies such as the Early Treatment Diabetic Retinopathy Study (ETDRS) and Age-Related Eye Disease Study (AREDS), whose work has literally defined many aspects of ophthalmology care and treatment.

The problem with using slide film as a "gold standard" color reference is that this film, especially Kodachrome, were often "warm" in tone and extremely high contrast. This is not a huge issue when photographing landscapes or portraits but is extremely problematic when reproducing medical subject matter (the retina) made up of mostly reds, oranges and yellows. While digital sensors are much more adept at preserving the relationship between colors, skewing the color profiles to replicate slide film technology is a recipe for warm toned, oversaturated, and high contrast images. (Hubbard et al., "Brightness, Contrast, and Color Balance of Digital Versus Film Retinal Images in the Age-Related Eye Disease Study 2," *Investigative Ophthalmology & Visual Science* 49(8):3269-82 (2008)). Any time the difference between tones is increased (by increasing contrast or saturation, or changing color balance), there is a tremendous risk for data loss, especially as it relates to subtle coloration.

The reason that an in-person examination is not necessarily a good color reference is two-fold: one is that the retina is being illuminated by a light source that is "warm" in tone, as many indirect ophthalmoscopes use tungsten or halogen light sources, incandescent sources which are around 3000 degrees Kelvin, resulting in a warm or orange cast to the light source and therefore the subject (newer indirect ophthalmoscope models may use an LED, which could prove to be far more color accurate). The second reason the retinal exam is not a good color reference has to do with the inability of the human observer to recall exact color. Since color is a product of perception created by our individual visual system, it is widely variable; additionally, the more time that has passed between an event and recalling that event, the more difficult it is for a human being to identify a color (or a color inaccuracy). (Bae et al., "Why Some Colors Appear More Memorable Than Others: A Model Combining Categories and Particulars in Color Working Memory," *J. Exp. Psychol. Gen.* 144(4):744-63 (2015)).

The color consistency problem in fundus imaging has not been resolved, which is why the FDA created a working group for Color in Medical Imaging. Considering the issue of color inconsistency has not been addressed broadly by the field, each manufacturer takes a different approach to calibrating (or not calibrating) color. The common denominator of a standard target would help to eliminate the disparity between color fundus imaging devices and provide color consistency that would aid in diagnosis and treatment of retinal disease.

SUMMARY

One aspect of the present technology relates to a color checker device. The color checker device includes a substrate configured to be inserted into a model eye and to conform to a surface curvature of the model eye when inserted therein. A color test target is located on the substrate. The color test target comprises a plurality of color sections configured for generating a color characterization profile of a fundus imaging camera configured to capture a color image of a human retina.

Another aspect of the present technology relates to a method of generating a color characterization profile of a fundus imaging camera configured to capture a color image of a human retina. The method includes receiving, by a computing device, an image of a model eye having a color checker device inserted therein captured by the fundus imaging camera. The color checker device comprises a substrate configured to be inserted into the model eye and to conform to a surface curvature of the model eye when inserted therein and a color test target located on the substrate. The color test target comprises a plurality of color sections configured for generating the color characterization profile of the fundus imaging camera. Color data in the received image is compared to known color data for the plurality of color sections in the color test target. The color characterization profile for the fundus imaging camera is generated based on the comparison between the color data in the received image to known color data for the plurality of color sections in the color test target.

Yet another aspect of the present technology relates to a fundus imaging system. The fundus imaging system includes a fundus imaging camera and a computing device comprising a processor and a memory, the memory having stored thereon a color characterization profile of a fundus imaging camera generated using an image of a model eye having a color checker device inserted therein. The color checker device comprises a substrate configured to be inserted into the model eye and to conform to a surface curvature of the model eye when inserted therein and a color test target located on the substrate. The color test target comprises a plurality of color sections configured for generating the color characterization profile of the fundus imaging camera. The processor is configured to receive an image of a human retina captured by the fundus imaging camera. The color characterization profile is applied to the received image to remove color bias of the fundus imaging camera.

The present technology provides a number of advantages including providing a customized color test target designed for use in the testing and calibration of the color for a fundus imaging system that includes a fundus imaging camera. The customized color target is configured to replicate the curvature of an emmetropic eye by conforming to the curved inner surface of a model eye and includes reference colors found in retinal imaging to mimic retinal imaging conditions. The color target can be used to generate a color characterization profile that can be used to correct color bias of a fundus imaging camera. The technology disclosed herein also provides a fundus imaging camera that includes a color characterization profile generated using the disclosed color target. Such a fundus imaging camera advantageously generates retinal images with a more standardized color output.

These and other aspects of the present disclosure will become apparent upon a review of the following detailed description and the claims appended thereto.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

The present disclosure relates to a color checker device for a fundus imaging camera. More specifically, the present disclosure relates to a color checker device configured for generating a color characterization profile of a fundus imaging camera configured to capture a color image of a human retina, a method of generating a color characterization profile using the color checker device, and a fundus imaging system having a color characterization profile generated using the color checker device stored thereon.

One aspect of the present technology relates to a color checker device. The color checker device includes a substrate configured to be inserted into a model eye and to conform to a surface curvature of the model eye when inserted therein. A color test target is located on the substrate. The color test target comprises a plurality of color sections configured for generating a color characterization profile of a fundus imaging camera configured to capture a color image of a human retina.

Figure 1:
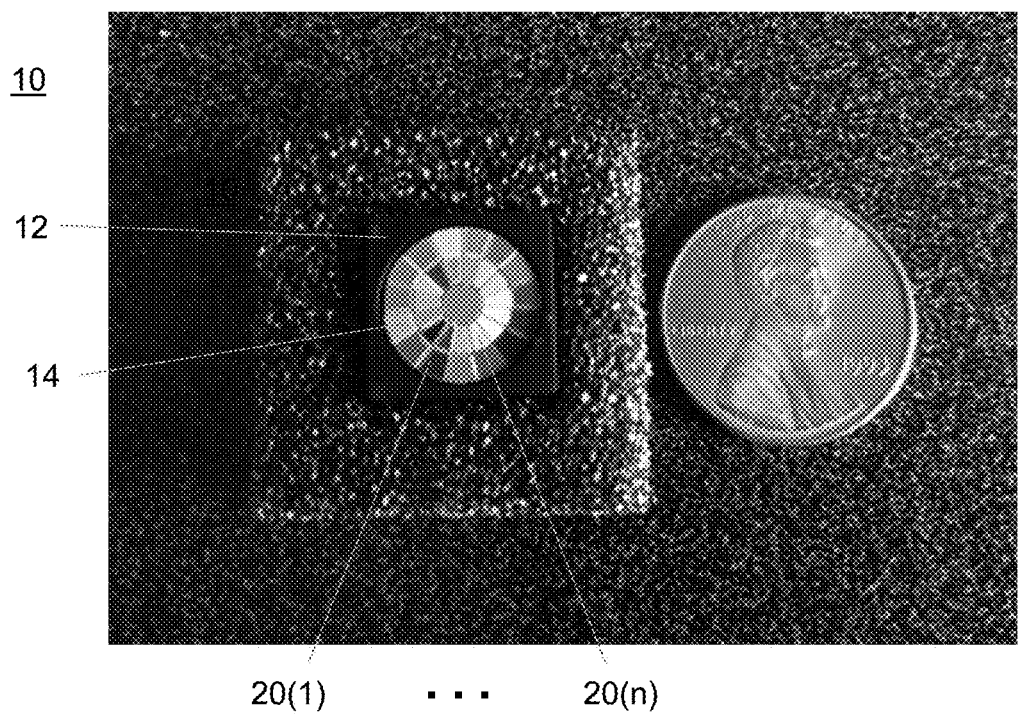
FIG. 1 illustrates an exemplary color checker device of the present technology.

FIG. 1 illustrates exemplary color checker device 10 of the present technology. Color checker device 10 includes a substrate 12 having a color test target 14 located thereon. Color checker device 10 provides a customized color test target designed for use in the testing and calibration of the color for a fundus imaging system. Color checker device 10 advantageously incorporates reference colors found in retinal imaging, is configured to be imaged by the standard "normal" viewing angle (magnification) of fundus imaging systems, and is configured to be applied to the inside of a model eye so that it can replicate the curvature of an emmetropic eye. These criteria ensure the target is being imaged in a manner that replicates the standard fundus imaging capture as closely as possible (replicating the conditions inside a human eye), while also taking into account the narrow color range and curved field of the human retina as the subject. Color checker device 10 can advantageously be used to generate a standard for both color reproduction and contrast in fundus imaging cameras for use by the ophthalmic imaging community, in order to bring these devices into greater levels of agreement and fidelity and standardize the color output of these devices.

Figure 2A:
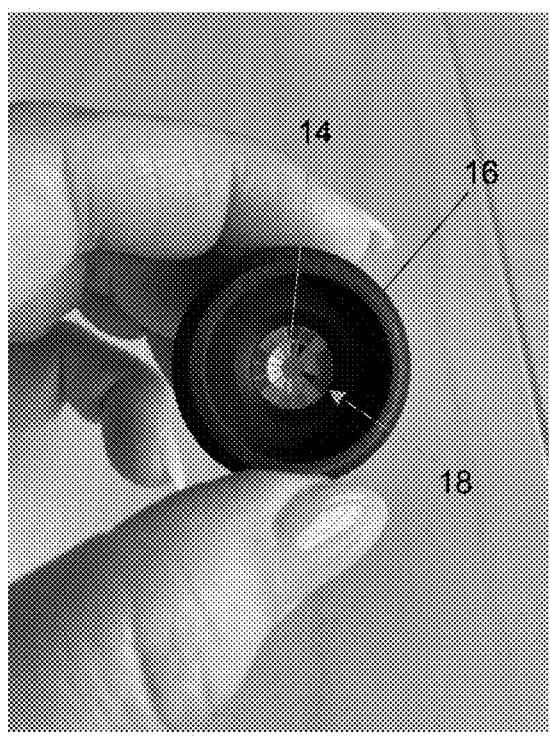
FIGS. 2A and 2B illustrate the exemplary color checker device of the present technology inserted into a model eye.
Figure 2B:
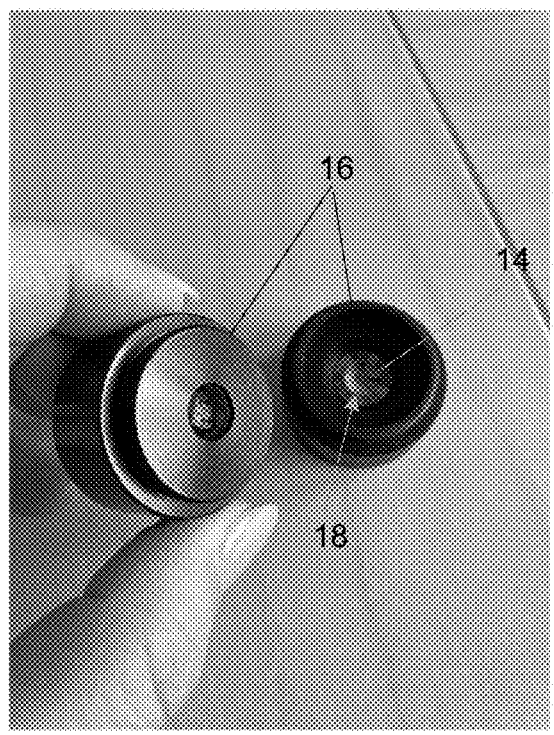

Referring again to FIG. 1, in this example substrate 12 is configured such that color checker device 10 can be utilized in a fundus imaging system. The fundus imaging system, for example, may include mydriatic and non-mydriatic fundus cameras, handheld and tabletop versions, or any device designed to create a color image of the human retina. Fundus imaging systems are designed in a manner such that the optics and curvature of the eye are employed as part of the imaging system. Substrate 12 is configured to be inserted into model eye 16 (as shown in FIGS. 2A and 2B). For purposes of this disclosure, a model eye includes any optical setup that allows for imaging of color checker device 10 under conditions that mimic the imaging of a human retina using a fundus imaging camera, including the field of view and magnification conditions as described in further detail below.

Figure 3:
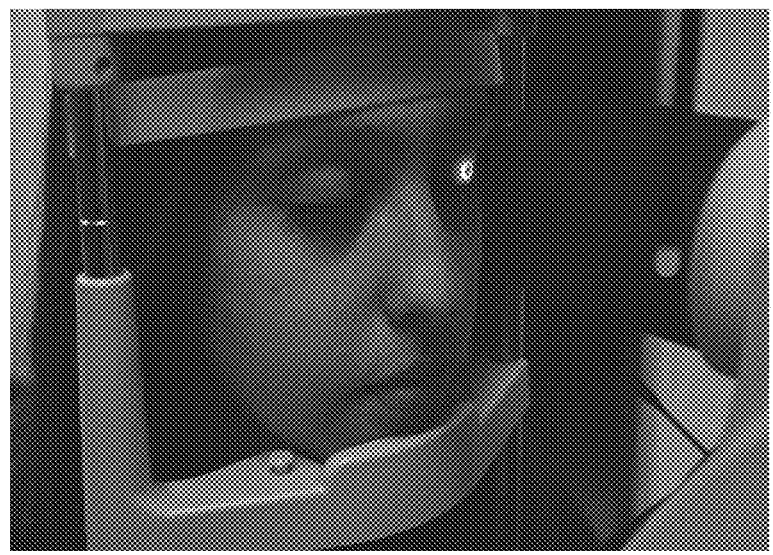
FIG. 3 illustrates a "donut" of axial illumination, shown on the patient's eyelid for visibility, employed in fundus imaging.
Figure 4:
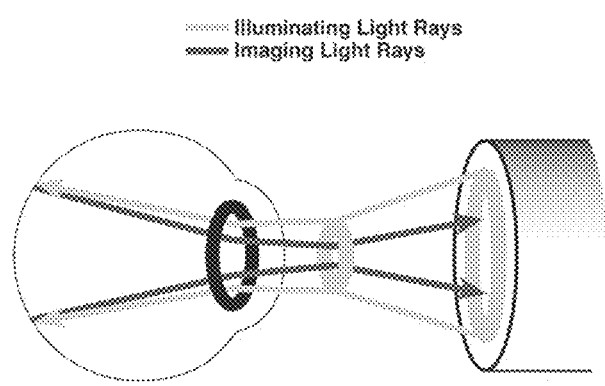
FIG. 4 illustrates the imaging and reflected light rays during fundus imaging.

In fundus photography, the donut shaped light source (emitted axially out of the lens objective used to capture the image) is directed through the front of the eye (the cornea), passes through the pupil, through the anatomical (or artificial) lens, to then spread and cover the retina as illustrated in FIG. 3. As illustrated in FIG. 4, the reflected light of the image then passes back out the pupil and through the donut "hole" (to avoid any reflection artifact from the cornea) to be captured by the sensor. In this manner, the eye is the other half of the optical system of the camera. This means that any refraction of the optical components of the eye (the cornea and lens), any media opacities, such as cataracts, corneal ulcers, or hemorrhages, will dictate the overall quality of the image. This is also why it is very difficult to separate out what color outcome is the result of the camera, and what is the result of the patient's eye.

For this reason, the color test target 14 of color checker device 10 of the present technology is configured to be photographed inside an optically accurate model eye, such as model eye 16 shown in FIGS. 2A and 2B, in order to accurately characterize the camera's behavior. The color checker device 10 must not only be small enough to be placed inside model eye 16, but the colors must not be printed using traditional methods, as the image magnification is significant, as discussed in further detail below. Additionally, the color test target 14 must replicate the curvature of the eye and retina, because the optics of fundus cameras are designed to capture that curved field. Photographing a flat object, such as a flat color checker, using a fundus imaging system, results in optical aberrations, including chromatic aberration that directly affects color. The color checker device 10 of the present technology reduces optical aberration in images of the color checker device 10 obtained by a fundus imaging camera.

Model eye 16 must provide an accurate model eye (one that best replicates the axial length and optical power of the average human eye) in order to replicate the conditions in which typical fundus photography is performed. Substrate 12 is sized to have a profile that allows insertion into model eye 16. In this example, substrate 12 is formed of a flexible plastic such that substrate 12 conforms to surface curvature 18 of model eye 16 when inserted therein as shown in FIGS. 2A and 2B, although substrate 12 may be formed of other suitable flexible materials.

Referring again to FIG. 1, color test target 14 is located on substrate 12 and is designed to be imaged within model eye 16 to best replicate the optical and physical conditions of imaging a human retina. Color test target 14 is configured to be imaged at a standard magnification of the fundus imaging camera when color checker device 10 is inserted in model eye 16 (as shown in FIGS. 2A and 2B), which averages around 2.5× life size.

Figure 5:
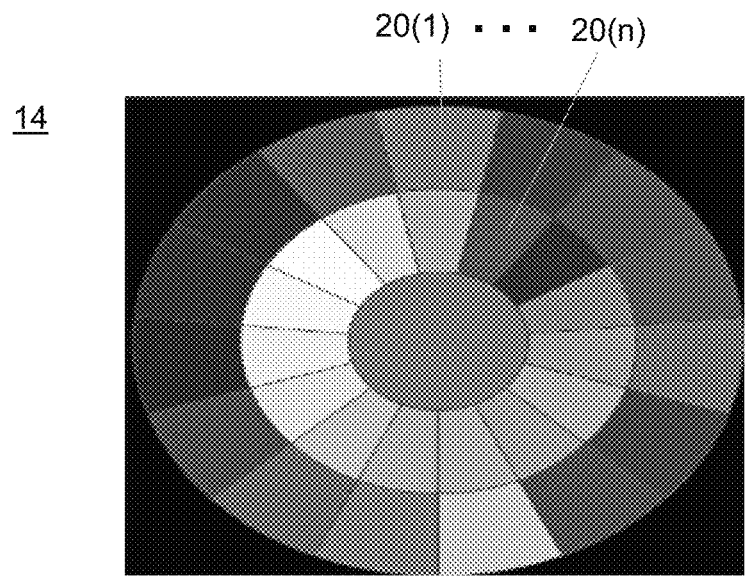
FIG. 5 illustrates an exemplary color test target of exemplary color checker device illustrated in FIG. 1.

Referring now to FIGS. 1 and 5, color test target 14 includes color sections 20(1)-20($n$) configured for generating a color characterization profile of a fundus imaging camera. For example, the color characterization profile may be a color bias profile for the fundus imaging camera, such as an International Color Consortium (ICC) profile, although other types of color characterization profiles may be generated. The color characterization profile is based on the difference between the color perceived by the fundus imaging camera in an image of color test target 14 obtained by the fundus imaging camera and the known color values for color sections 20(1)-20($n$). In this manner, the color characterization profile is configured to correct the color generated by the fundus imaging camera during subsequent retinal imaging to remove any color bias imparted by the fundus imaging camera. This provides more consistency in the color representation of retinal images. In this example, the color characterization profile is generated using colors directly related to retinal imaging as described below, which improves consistency in the color correction when performing retinal imaging. Color sections 20(1)-20($n$) are sized to provide enough surface area to test, but also to fit inside a standard angle of view on a fundus imaging camera, typically 35-40 degrees.

In this example, color sections 20(1)-20($n$) are arranged in a pair of circular rings on substrate 12, although other configurations for color sections 20(1)-20($n$). This configuration of color sections 20(1)-20($n$) allows for a larger number of color sections to be located on substrate 12, which is sized to be located in model eye 16. The use of a greater number of reference colors provides for more contrast, which in turn provides a more accurate color characterization profile. In one example, at least 31 color sections are employed with unique reference colors, although other numbers of color sections are contemplated.

Figure 6A:
FIG. 6A illustrates the circular/truncated circle of a fundus image that is typically captured by both mydriatic and non-mydriatic fundus cameras.
Figure 6B:
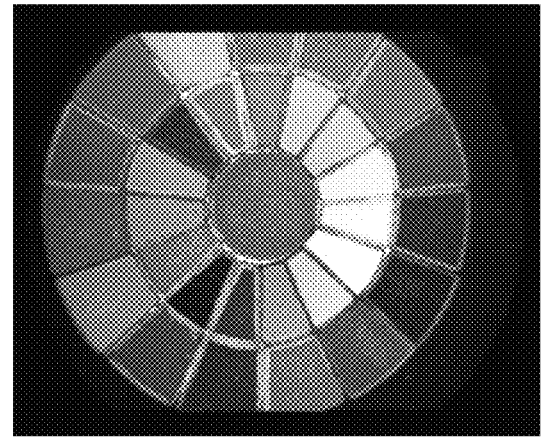
FIG. 6B shows an image of the color test target of the exemplary color checker device of FIG. 1 imaged inside a model eye on a mydriatic fundus camera at a 30-degree field of view.

The circular configuration further allows color test target 14 to fit best in the traditional circular/truncated circle of a fundus image that is typically captured by both mydriatic and non-mydriatic fundus cameras as illustrated in FIG. 6A. FIG. 6B illustrates an exemplary image of color test target 14 of color checker device 10 of FIG. 1 imaged inside a model eye on a mydriatic fundus camera at a 30-degree field of view.

Referring again to FIGS. 1 and 5, in this example, color sections 20(1)-20($n$) of color test target 14 are painted on substrate 12. The use of painted color sections are both a photographic color management standard and allows for a better mathematical representation of the colors when imaged under magnification (typically around 2.5× life size for a fundus imaging camera), as opposed to printed colors, which result in individual dots of inks being visible when imaged under magnification typically used in fundus imaging.

Color test target 14 includes color sections 20(1)-20($n$) that have unique color values. The color values for color sections 20(1)-20($n$) include colors that are typical to any optical imaging system and imaging standards, but also include reference colors from representative colors found in the retina, including variation in pigmentation, colors found in retinal disease signs and symptoms, and a scale to evaluate the gamma or contrast of the device. Retinal color varies by ethnicity, so the colors included are represented by the variety of reds, oranges and browns found among these populations, by way of example.

Color sections 20(1)-20(n) include one or more anchor colors and a plurality of retinal reference colors that are representative of colors found in the human retina. The one or more anchor colors are representative of reference colors standard to the fundus imaging camera. The plurality of retinal reference colors comprise at least a first set of colors representative of variations in pigmentation in the human retina. The variations in retinal pigmentation are based on ethnicity, but can also result from disease or injury. The plurality of retina reference colors further include a second set of colors representative of retinal disease signs and symptoms in the human retina. These include intraretinal, subretinal and vitreous hemorrhages, scar tissue (fibrosis), cotton wool spots, exudates, drusen, and hyper or hypopigmentation, by way of example only.

As discussed above, color sections 20(1)-20(n) include representative colors that occur in the retina due to variation in pigment and retinal disease. Since the sensors used in fundus imaging cameras are standard digital photography color sensors (CCD or CMOS with a Bayer color filter array to capture color), they are designed to capture the rainbow of the visible spectrum. Using these sensors to image the retina means the fundus imaging cameras are only utilizing a very small portion of its total color capability, while also not optimizing the colors reproduced in a retinal image. The retina is a narrow gamut subject and profiling the camera to take this into consideration optimizes the sensor for the subject it is being used to capture. The use of reference colors related to color variations typically found in a human retina allows for a more accurate profiling of the camera's color behavior.

Figure 7:
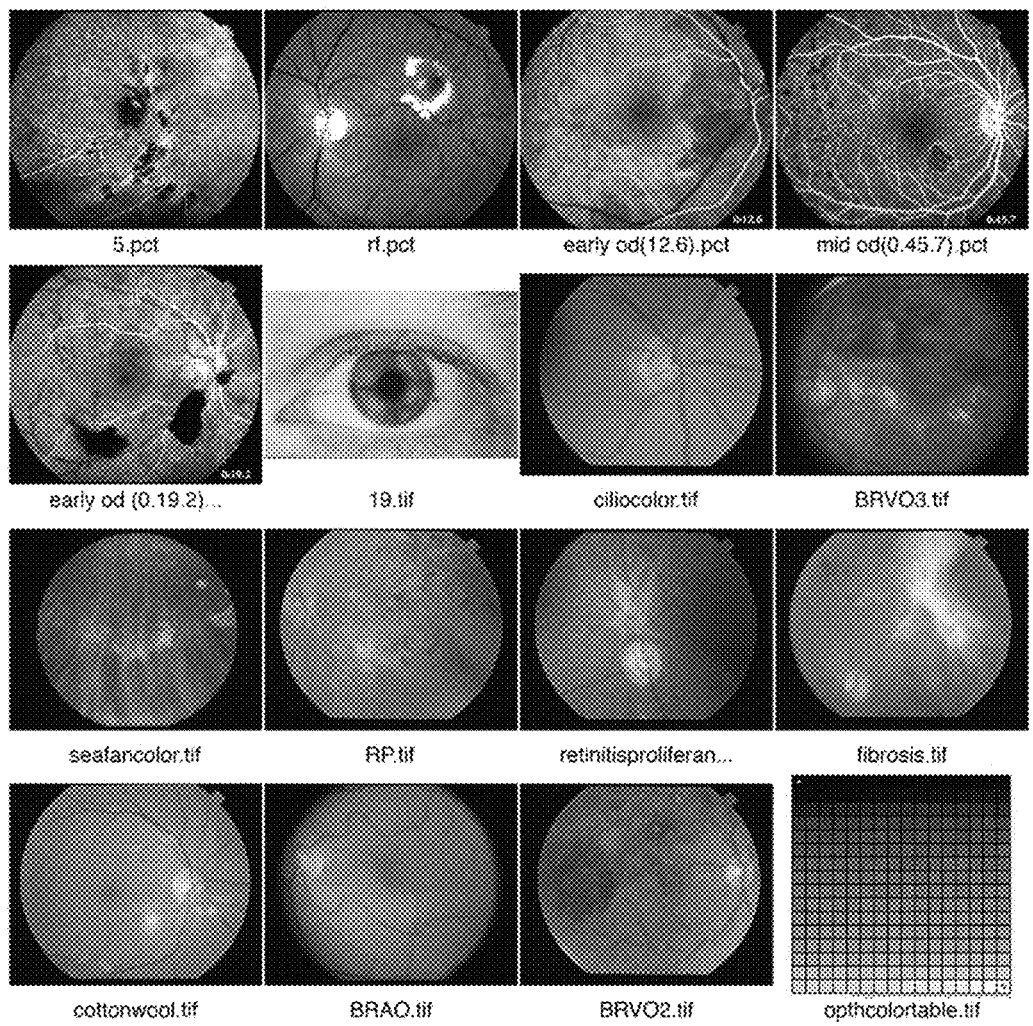
FIG. 7 illustrates a plurality of retinal images captured using a fundus imaging having various representative colors and a color table (lower right-hand image) generated using the representative colors.

In one example, retinal representative colors were found by sampling a variety of colors found among retinas with different pigmentation (variation determined by ethnicity), as well as representative colors found in different retinal disease signs and symptoms, including a variety of hemorrhage types, abnormal pigmentation, scar tissue (fibrosis), drusen and other retinal disease markers. FIG. 7 illustrates various representative colors in retinal images obtained using a fundus imaging camera. These include variation in background pigment (ex. Seafancolor.tif compared to RP.tif compared to retinitisproliferans.tif), coloration in abnormal pigmentation (RP.tif), variation in hemorrhage (BRVO3.tif, retnitisproliferans.tif, BRVO2.tif), and lighter areas characteristic of edema (BRAO.tif), cotton wool spots (cottonwool.tif), exudates (BRVO3.tif) and scar tissue (fibrosis.tif). FIG. 7, in the bottom right hand image, also illustrates a color table generated from the representative colors obtained from the images in FIG. 7.

While all photographic sensors are designed to reproduce a rainbow of colors, optimizing a sensor used for a particular (and smaller) range of colors, such as the retinal representative colors illustrated in the color table of FIG. 7, will provide the best opportunity to maintain detail, and most importantly, differences between those colors. By including these retinal reference colors (along with the anchor colors described above) in the color checker device 10, it is ensured that the color characterization profile generated using the color checker device 10 (as described in the method below) reproduces and prioritizes these specific retinal reference colors. These colors, in one example, are referenced by analyzing a collection of retinal images, but also by prioritizing critical differences in values, for example highlight values in the optic nerve head, to ensure those differences are maintained.

Another aspect of the present technology relates to a method of generating a color characterization profile of a fundus imaging camera configured to capture a color image of a human retina. The method includes receiving, by a computing device, an image of a model eye having a color checker device inserted therein captured by the fundus imaging camera. The color checker device comprises a substrate configured to be inserted into the model eye and to conform to a surface curvature of the model eye when inserted therein and a color test target located on the substrate. The color test target comprises a plurality of color sections configured for generating the color characterization profile of the fundus imaging camera. Color data in the received image is compared to known color data for the plurality of color sections in the color test target. The color characterization profile for the fundus imaging camera is generated based on the comparison between the color data in the received image to known color data for the plurality of color sections in the color test target, a standard methodology in color management practices.

Figure 8:
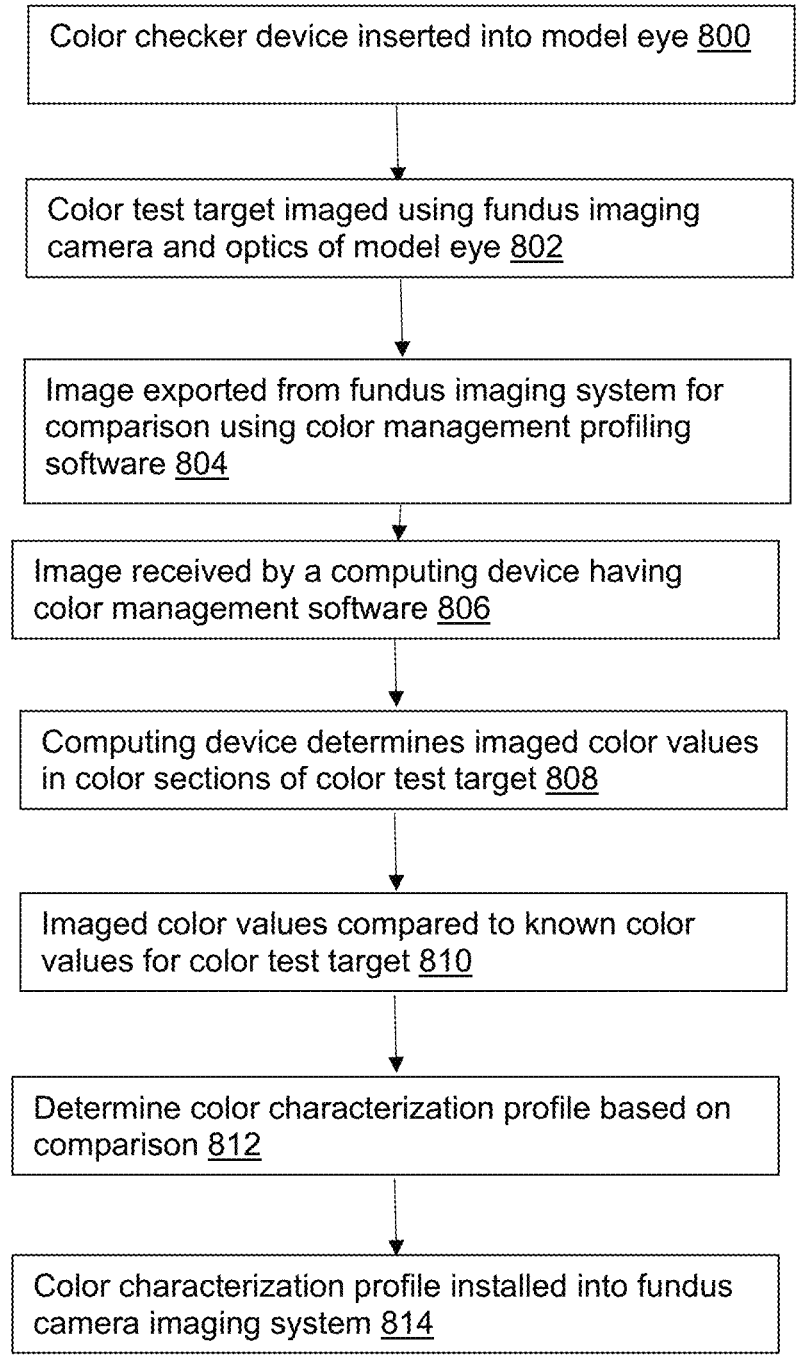
FIG. 8 is a flow chart for an exemplary method of generating a color characterization profile for a fundus imaging camera of the present technology.

FIG. 8 illustrates an exemplary method of generating a color characterization profile for a fundus imaging camera configured to capture a color image of a human retina using the color checker device 10 of the present technology. In step 800, color checker device 10 is inserted into model eye 16 as illustrated in FIGS. 2A and 2B. As described above, model eye 16 must be an accurate model eye (one that best replicates the axial length and optical power of the average human eye) in order to replicate the conditions in which typical fundus photography is performed. Substrate 12 is sized to have a profile that allows insertion into model eye 16 and conforms to surface curvature 18 of model eye 16 when inserted therein as shown in FIGS. 2A and 2B.

Next, in step 802 color checker device 10, which includes color test target 14, is imaged using a fundus imaging system or camera configured to capture an image of a human retina. The fundus imaging system, for example, may include mydriatic and non-mydriatic fundus cameras, handheld and tabletop versions, or any device designed to create a color image of the human retina. In one example, the image of color test target 14 is obtained using a "middle" or "normal" angle of view of the fundus imaging system, typically a 30-40 degree field of view. Proper alignment, working distance, and focus should be established as known in the art of retinal imaging prior to obtaining the image. Further, in one example viewing illumination is reduced prior to obtaining the image as viewing illumination has been found to influence color temperature significantly and with great variability. Accordingly, reducing viewing illumination provides for more accurate color characterization in the present method. In one example, the image of color test target 14 obtained is a substantially "normal" exposure, meaning the values in the exposure best reflect the values in the original target subject.

In step 804, the image of color test target 14 is exported from the funding imaging system or camera for comparison using a color management profiling software as described below.

In step 806, the image of color test target 14 is received by a computing device having color management software stored thereon that describes color between devices. For example, the computing device described below with respect to an exemplary fundus imaging system may be employed. Examples of CMS include Kodak CMS, Efi-Color, Agfa FotoFlow, and the Pantone Open Color Environment. All of these systems use a color profile having target colors to describe the color behavior of each input/output device. However, the profile must first be generated before it can be imported into the CMS. There are a variety of color management software solutions (eg., Xrite, Color-Munki, Adobe Lightroom) that compare the target colors to the colors obtained by the device in order to generate a profile.

In step 808, the color values for color sections 20(1)-20(n) in the received image of color test target 14 are determined by the computing device. The determined color values have the color bias imparted by the fundus imaging system. The determined color values include colorimetric data in RGB and CIELAB values, by way of example.

Figures 12A, 12B:
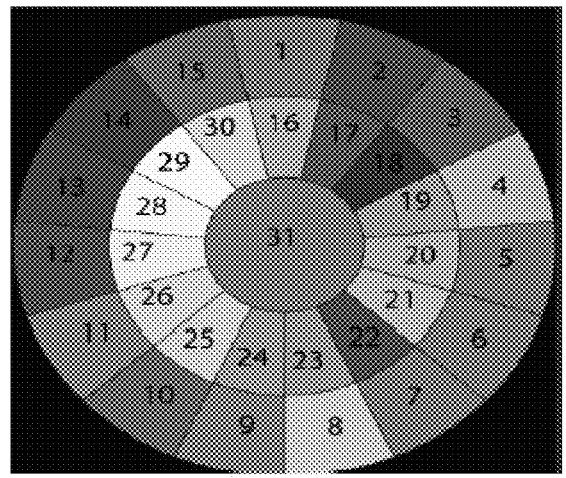
FIG. 12A illustrates an exemplary color test target of the disclosed technology.
FIG. 12B illustrates spectral data for the plurality of color sections in the color test target shown in FIG. 12A.

In step 810, the imaged color values determined in step 806 are compared to known reference or target color values for color sections 20(1)-20(n) in color test target 14. For example, FIG. 12A illustrates an exemplary color checker device having the known spectral data illustrated in FIG. 12B. Color checker device 10 provides custom color test target 14 for use in imaging according to the standards created for existing photographic color checkers. Referring to FIGS. 1 and 5, color checker device 10 includes color test target 14 having color sections 20(1)-20(n) that provide calibrated color patch samples with known reference or target color values for the color sections 20(1)-20(n), including colorimetric data in RGB and CIELAB values. In one example, the obtained image color values can be subtracted from the known reference color values, using color management software, to identify any color disparities for the fundus imaging system or camera.

In step 812, the color characterization profile for the fundus imaging camera is generated based on the comparison between the color data or values for color sections 20(1)-20(n) in the obtained image to known color data for color sections 20(1)-20(n) in color test target 14. In one example, the disparities in the color values are output using the color management software to generate the color characterization profile for the fundus imaging camera, such as an International Color Consortium (ICC) profile, which can then be input back into the capture software of the fundus imaging camera to help standardize the color behavior of the fundus imaging camera as described below.

In step 814, the color characterization profile, describing fundus camera behavior, is installed into fundus camera imaging system to be referenced by the systems color management system (CMS) to describe and account for the camera's color behavior during operation. The color characterization profile can be used by the fundus imaging camera used to obtain the image in step 802. Alternatively, the color characterization profile can be used in fundus imaging cameras that are similar in operation, such as fundus imaging cameras that are the same model as the fundus imaging camera used to obtain the image in step 802. Once the color characterization profile is stored on the fundus imaging camera, the color characterization can be used to correct image bias from the fundus imaging camera in obtained images. The color characterization profile can also be stored along with the image data for each obtained image. This increases the likelihood that the image will appear similar in color when displayed on other devices despite the color limitations of such devices.

An example use of the method of generating a color characterization profile disclosed herein is in the testing and potential certification of fundus imaging devices to standardize the color output of these devices. This certification could take place at the manufacturer level or be performed by reading centers interested in bringing the devices certified for studies within a known color standard.

Figure 9:
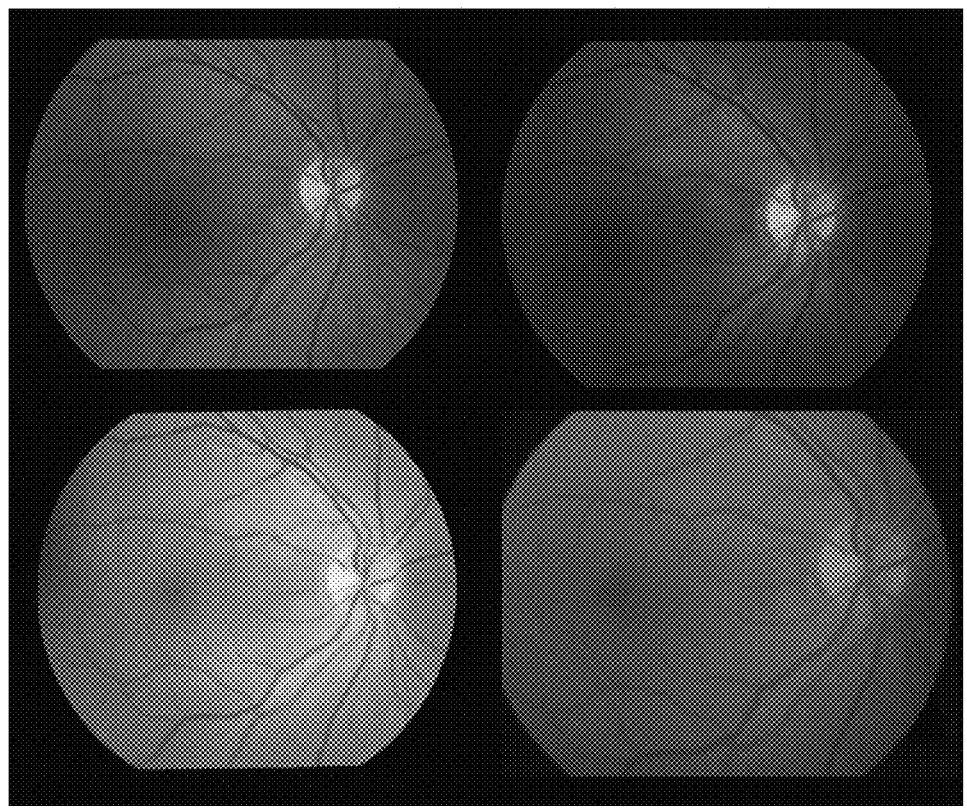
FIG. 9 illustrates the disparity in color image results for the same patient imaged using four different fundus imaging cameras from the same manufacturer.

Another exemplary use of the disclosed technology is to provide a standard for both color reproduction and contrast for use by the ophthalmic imaging community, in order to bring these devices into greater levels of agreement and fidelity. FIG. 9 illustrates the disparity in color image results for the same patient imaged using four different fundus imaging cameras, including two from the same manufacturer.

A color characterization profile, such as an ICC camera profile, is generated which then could be applied via the image capture software to remove any color or contrast biases from the system. Once these profiles were generated, they could be generalized to be applied to all of the device models (i.e., a particular fundus camera make/model) using the same components, resulting in consistent color and contrast from device to device, and ideally, adopted by all manufacturers of fundus cameras, so that all devices in the field conform to this standard. This is the current color standardization model used in commercial digital photography; all capture devices, from cameras to scanners to printers, come with built-in ICC profiles to describe the color behavior of each device. The software then integrates this behavior as a reference of understanding between devices to allow for greater color consistency between devices.

This consistency would result in a much more of an "apples to apples" fundus image comparison because all of the cameras would be brought into at least a baseline level of color agreement. This would also help to identify any color anomalies outside the camera/imaging system, such as lens opacities or other media obstructions in the patient's eyes that are not uncommon to diseased eyes. This baseline would potentially lead to greater levels of disease detection and identification, particularly in the context of the image standing in place of a physical retinal exam.

Color and contrast are essential in identifying retinal disease. Ophthalmologists and other eye care professionals are trained to identify signs and symptoms of retinal disease based upon the physical features and characteristics of those diseases as they appear in the retina. These might include hemorrhages (blood) at different levels of the retina (which are often differentiated by color), retinal anomalies such as cotton wool spots (whitish areas indicating ischemia), drusen (patches indicating aging or accelerated deterioration, such as in age-related macular degeneration), or exudative changes (yellowish blobs of partially metabolized fluid, indicating leakage). Further, optic nerve head disorders, such as optic atrophy, are often identified by the pallor, or paleness, of the optic nerve as compared to normal.

In an ophthalmology setting, all of these potential indicators would be followed by expanded testing to confirm a suspected diagnosis. But in that same setting, these signs are most often found through retinal exam, not by retinal imaging; the imaging is performed as a record of what the patient's eye looked like today for comparison after treatment. In the case where the imaging is standing in place of an-in person exam, the images are the only record of the retinal appearance, and a too-contrasty image can be diagnosed with optic atrophy, or an overly saturated, too red image, might obscure the tell-tale tiny hemorrhages characteristic of diabetic retinopathy.

The implication of this level of standardization would most notably impact two fields: imaging research (reading centers where they collect retinal images collected over time for clinical studies among diverse populations and locations) and tele-health, specifically teleophthalmology. Since both of these fields use the images of the retina to act as a patient proxy, and do not allow for live, in-person patient examination for comparison, the image consistency becomes that much more crucial in order to make a diagnosis, or even to determine the presence of disease. Given the level of importance to image quality in both of these circumstances, the repeatable, reliable results of these imaging devices become that much more critical.

As health care monitoring and technology becomes increasingly miniaturized, combined with the increasing aggregation of health data via mobile devices, there are technologies actively being pursued in the ophthalmology space to design small, portable, and potentially self-administered methods of capturing retinal images. Retinal images have long been known to be a literal window into the overall health and wellness of a patient and can indicate signs of systemic disease in the cardiovascular or metabolic systems, such as high blood pressure or diabetes.

Further, deep learning systems are being employed to identify patterns in these images less obvious to a human observer, as evidenced in studies being conducted on automated evaluation of color retinal images for disease. (Lim et al., "A Deep Learning Algorithm to Detect Chronic Kidney Disease From Retinol Photographs in Community-Based Populations," *Lancet Digital Health* 2:e295-301 (2020))

The first step in the widespread use of these images to monitor overall patient health and wellness is the standardization of what those images mean in terms of outcome. For any of these images to be used for diagnostic purposes, the tonal reproduction of the retina needs to be as consistent as possible from device to device to accurately assess patient features, either by a human observer or in a machine vision system.

It is exceedingly rare that the engineers who are designing and implementing these fundus imaging systems are knowledgeable about photographic color management. These cameras have not fundamentally changed in design since using film, other than including a digital camera and software to view the images. Additionally, ophthalmologists have never asked for such color calibration. There are a few reasons for this; one, it is unheard of to photograph a patient on more than one version of the same device per visit, so drawing a direct comparison of the same eye on multiple cameras is not usually done, even if the clinic has more than one camera. The second reason is that ophthalmologists rely more on the physical retinal examination than the images in the ophthalmology clinic; these doctors are the primary purchasers of this equipment, and use these color images in the clinical context as patient records, not necessarily to determine a diagnosis.

Additionally, trying to perform a characterization of these devices by replicating all of the variables associated with capturing an image through a patient's eye, is not a simple procedure. This effort must replicate as closely as possible these imaging conditions in order to provide an accurate representation of the camera's color and contrast response. In other words, a target can't simply be photographed in front of the camera; and it has to take into account the curved nature of the subject, the position of the retina behind two refractive surfaces (the cornea and the lens) and the specialized colors and narrow gamut of the subject.

However, these same cameras are also used for clinical trial/research imaging (often within the ophthalmology clinic). Ophthalmology clinics and practices often engage in clinical trials, whereby the retinal images are studied from a cross-section of patients over time for a particular disease or pharmaceutical study. These images are then sent to a research/reading center for those images to be graded for quality, and then "read" for a variety of features, depending on the study. Studies will vary widely in terms of the features they are looking to identify, from broad signs to specific details, and the color and contrast of a camera directly impacts that ability. For example, for an optic nerve head study, a patient's optic nerve can be completely "blown out" or devoid of detail if the contrast is set too high on the camera, but an ophthalmologist reading that image could interpret that pale disc as disc pallor, and determine the patient has optic atrophy or similar condition.

Similarly, the color can influence the interpretation of the image as well. For example, if a study needs to count dot and blot hemorrhages/microaneurysms (signs associated with Diabetic Retinopathy), the subtle red freckling can be lost if the saturation of the image is too high, or if the image is too yellow/red.

Teleophthalmology is the other field affected by this lack of calibration. Since those images also stand in place of an ophthalmologists' physical retinal exam, the image quality becomes of paramount importance to identify the signs and symptoms of retinal disease. The above examples are two such representative diseases that could be missed or misdiagnosed due to color and contrast inconsistency in imaging. Since the same cameras that are manufactured for the ophthalmic imaging clinics are also used in this context, they have the same issues and variability of color/contrast.

Yet another aspect of the present technology relates to a fundus imaging system. The fundus imaging system includes a fundus imaging camera and a computing device comprising a processor and a memory, the memory having stored thereon a color characterization profile of a fundus imaging camera generated using an image of a model eye having a color checker device inserted therein. The color checker device comprises a substrate configured to be inserted into the model eye and to conform to a surface curvature of the model eye when inserted therein and a color test target located on the substrate. The color test target comprises a plurality of color sections configured for generating the color characterization profile of the fundus imaging camera. The processor is configured to obtain an image of a human retina captured by the fundus imaging camera. The color characterization profile is applied to the obtained image to remove color bias of the fundus imaging camera.

Figure 10:
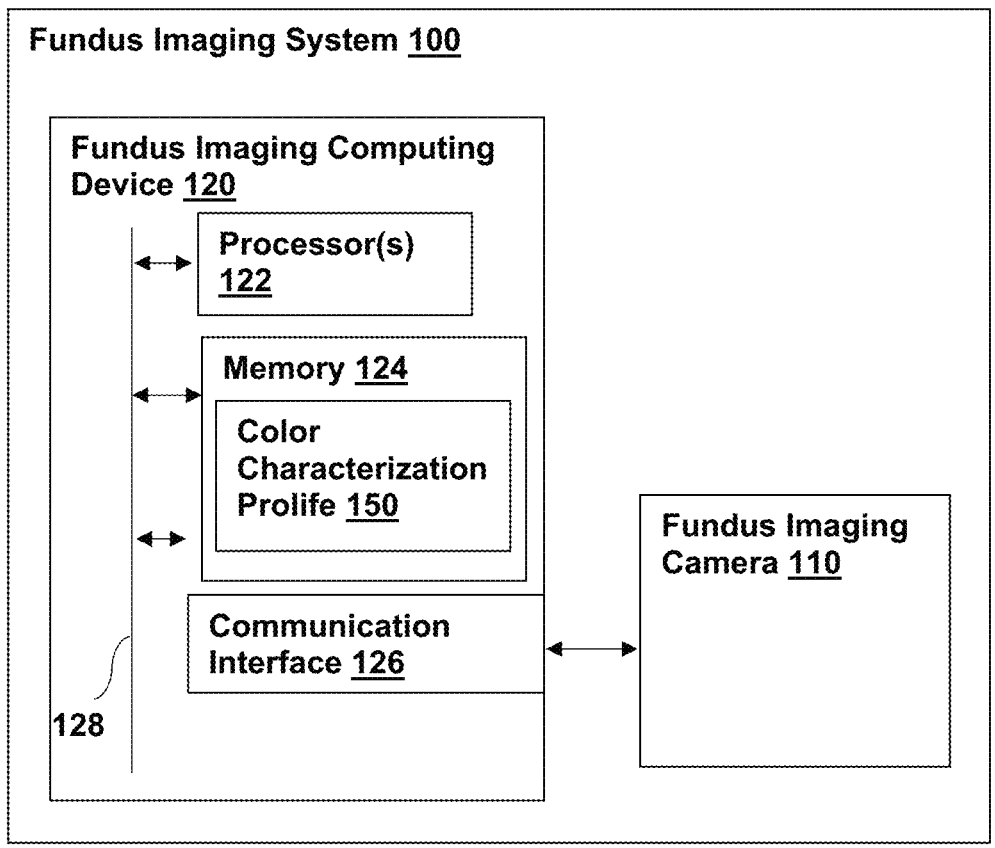
FIG. 10 is a block diagram of a fundus imaging system employing a color characterization profile generated in accordance with the methods of the present technology.

FIG. 10 is a block diagram of an exemplary fundus imaging system 100 incorporating the present technology. In this example, fundus imaging system 100 includes fundus imaging camera 110 and fundus imaging computing device 120, although the fundus imaging system 100 can include other types and or numbers of elements in other combinations. Fundus imaging camera 110 and fundus imaging computing device 120 can be separate devices communicatively coupled by a communication network or can be part of a single device.

Fundus imaging camera 110 is a camera device configured to capture an image of a human retina. The fundus imaging camera 110, for example, may include mydriatic and non-mydriatic fundus cameras, handheld and tabletop versions, or any device designed to create a color image of the human retina. Example fundus imaging cameras include Canon (Tokyo, Japan) Model CF60-Uvi, Topcon (Tokyo, Japan) Model TRC-50EX, Topcon (Tokyo, Japan) Model TRC-50DX, and Zeiss (Jena, Germany) Model FF450plus.

Fundus imaging computing device 120 includes one or more processor(s) 122, a memory 124, and a communication interface 126, which are coupled together by a bus 128 or other communication link, although fundus imaging computing device 120 can include other types and/or numbers of elements in other configurations.

Processor(s) 122 of fundus imaging computing device 120 may execute programmed instructions stored in memory 124 for any number of the functions described and illustrated herein. In one example, processor(s) 122 obtain and process images from fundus imaging camera 110. Processor(s) 122 may include one or more CPUs, GPUs, or general purpose processors with one or more processing cores, for example, although other types of processor(s) can also be used such as FPGA devices.

Memory 124 stores these programmed instructions for one or more aspects of the present technology as described and illustrated herein, although some or all of the programmed instructions could be stored elsewhere. A variety of different types of memory storage devices, such as random access memory (RAM), read only memory (ROM), hard disk, solid state drives, flash memory, or other computer readable medium which is read from and written to by a magnetic, optical, or other reading and writing system that is coupled to the processor(s), can be used for the memory.

Accordingly, memory 124 of fundus imaging computing device 120 can store one or more applications or programs that can include computer executable instructions that, when executed by processor(s) 124 of fundus imaging computing device 120, cause fundus imaging computing device 120 to perform actions described below. The application(s) can be implemented as modules, threads, pipes, streams, or components of other applications. Further, the application(s) can be implemented as operating system extensions, module, plugins, or the like. In this example, memory 124 includes color characterization profile 150 generated for the fundus imaging camera 110 in accordance with the methods described herein. Color characterization profile 150 is configured to correct for a color bias of the fundus imaging camera 110, by way of example. In one example, color characterization profile 150 is generated using fundus imaging camera 110 employing the methods described herein. In another example, color characterization profile 150 is generated by the manufacturer using the methods disclosed herein and is applied to fundus imaging cameras of the same model, or using the same imaging devices.

Even further, the application(s) may be operative in a cloud-based computing environment. The application(s) can be executed within or as virtual machine(s) or virtual server(s) that may be managed in a cloud-based computing environment. Also, the application(s) may be running in one or more virtual machines (VMs) executing on fundus imaging computing device 120. Communication interface 126 operatively couples and communicates between fundus imaging computing device 120 and fundus imaging camera 110. For example, fundus imaging computing device 120 can be configured to obtain and process fundus images obtained by fundus imaging camera 110. More specifically, fundus imaging computing device 110 is configured to provide color correction of images obtained by fundus imaging camera 110 by applying color characterization profile 150 to remove color bias from the obtained images.

Although exemplary fundus imaging computing device 120 is described and illustrated herein, other types and/or numbers of systems, devices, components, and/or elements in other topologies can be used. It is to be understood that the systems of the examples described herein are for exemplary purposes, as many variations of the specific hardware and software used to implement the examples are possible, as will be appreciated by those skilled in the relevant art(s).

In addition, two or more computing systems or devices can be substituted for fundus imaging computing device 120. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including by way of example only teletraffic in any suitable form (e.g., voice and modem), wireless traffic networks, cellular traffic networks, Packet Data Networks (PDNs), the Internet, intranets, and combinations thereof.

The examples may also be embodied as one or more non-transitory computer readable media having instructions stored thereon for one or more aspects of the present technology as described and illustrated by way of the examples herein. The instructions in some examples include executable code that, when executed by one or more processors, cause the processors to carry out steps necessary to implement the methods of the examples of this technology that are described and illustrated herein.

EXAMPLES

Example 1—Prototype

A prototype color checker device was constructed that included 31 patches of color, including 6 legacy colors (RGBCMY from XRite CC 24), 5 neutral/greyscale, and the remaining 20 custom retinal colors selected from a custom LUT (lookup table) generated by sampling 20 various retinal images, such as the images illustrated in FIG. 7. These color patches were mounted circularly on a substrate of clear, flexible acetate, to allow the target to conform to the inner curvature of a model eye.

Figure 11:
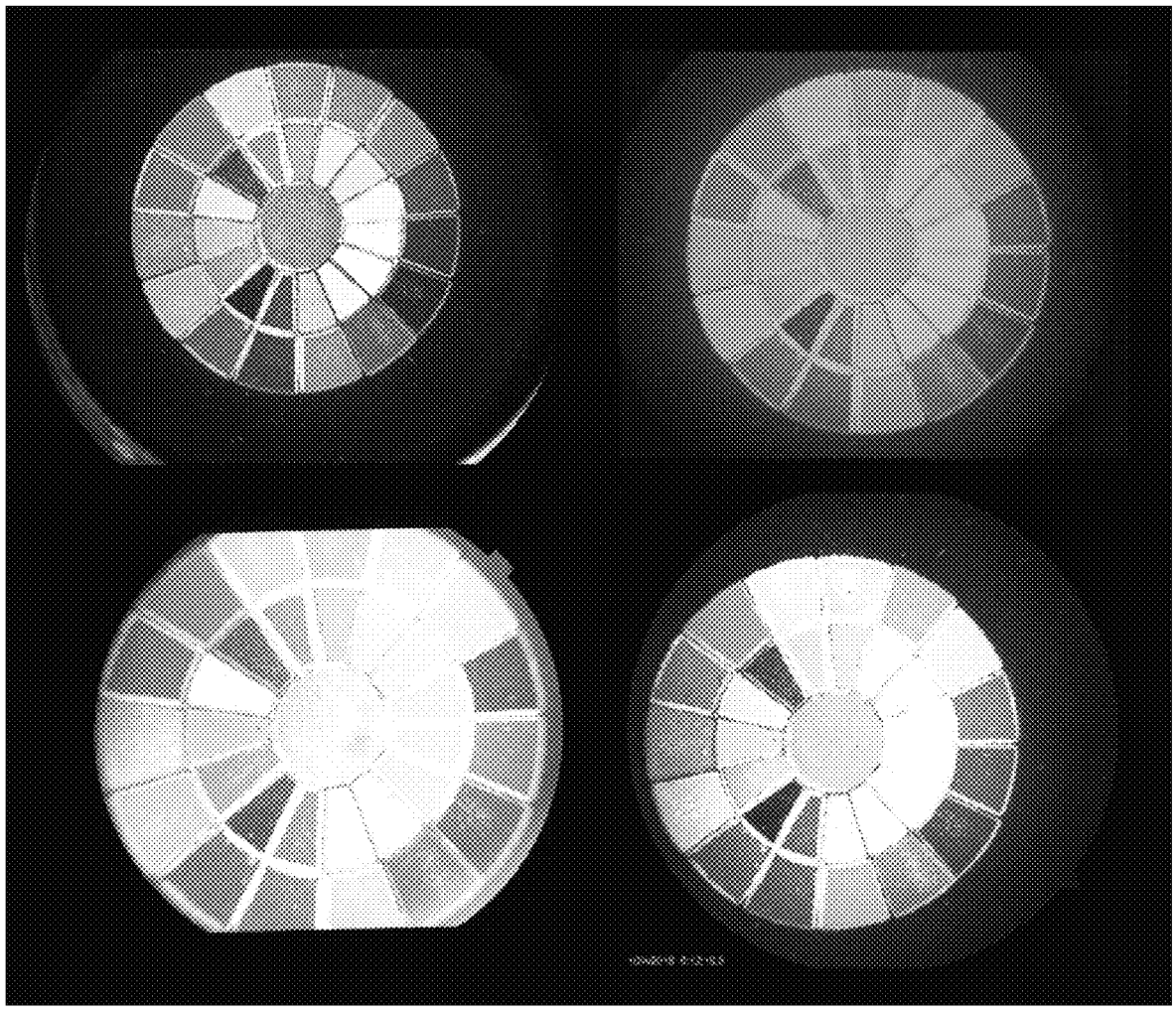
FIG. 11 illustrates images obtained of a prototype color checker device photographed inside a model eye using four different fundus imaging cameras.

FIG. 11 illustrates images obtained of the prototype photographed inside a model eye using four different fundus imaging cameras. The curved field significantly reduced optical aberrations. The size and shape of the device worked with a variety of magnifications.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. A color checker device comprising:
   a substrate configured to be inserted into a model eye and to conform to a surface curvature of the model eye when inserted therein; and
   a color test target located on the substrate, wherein the color test target comprises a plurality of painted color sections, each section having a different color that is represented in a human retina, which when imaged under magnification by a fundus imaging camera provides a mathematically represented painted color absent individual dots of ink being visible and generates color data for a color characterization profile of the fundus imaging camera.

2. The color checker device of claim 1, wherein the plurality of color sections are configured to generate a color bias profile for the fundus imaging camera.

3. The color checker device of claim 2, wherein the plurality of color sections include one or more anchor colors and a plurality of retinal reference colors that are representative of colors found in the human retina.

4. The color checker device of claim 3, wherein the plurality of retinal reference colors comprise at least a first set of colors representative of variations in pigmentation in the human retina and a second set of colors representative of retinal disease signs and symptoms in the human retina.

5. The color checker device of claim 4, wherein the variations in pigmentation are based on age, ethnicity, or disease factors.

6. The color checker device of claim 3, wherein the one or more anchor colors are representative of reference colors standard to the fundus imaging camera.

7. The color checker device of claim 1, wherein the color test target is configured to be imaged at a standard magnification of the fundus imaging camera.

8. A method of generating a color characterization profile of a fundus imaging camera configured to capture a color image of a human retina, the method comprising:
receiving, by a computing device, an image of a model eye having a color checker device inserted therein captured by the fundus imaging camera, wherein the color checker device comprises a substrate configured to be inserted into the model eye and to conform to a surface curvature of the model eye when inserted therein and a color test target located on the substrate, wherein the color test target comprises a plurality of color sections configured for generating the color characterization profile of the fundus imaging camera;
comparing, by the computing device, color data in the received image to known color data for the plurality of color sections in the color test target; and
generating, by the computing device of the fundus imaging system, the color characterization profile for the fundus imaging camera based on the comparison between the color data in the obtained image to known color data for the plurality of color sections in the color test target.

9. The method of claim 8, wherein the image is captured by the fundus imaging camera at a reduced viewing illumination.

10. The method of claim 8, wherein the image is captured by the fundus imaging camera at a normal angle of view.

11. The method of claim 8, wherein the image is captured by the fundus imaging camera at substantially a normal exposure level.

12. The method of claim 8, wherein the generating comprises subtracting the color data in the obtained image from the known color data for the plurality of color sections in the color test target to determine the color characterization profile for the fundus imaging camera.

13. The method of claim 8, wherein the plurality of color sections on the color checker device are painted on the substrate.

14. The method of claim 8, wherein the plurality of color sections on the color checker device are configured to generate a color bias profile for the fundus imaging camera.

15. The method of claim 14, wherein the plurality of color sections on the color checker device include one or more anchor colors and a plurality of retinal reference colors that are representative of colors found in the human retina.

16. The method of claim 15, wherein the plurality of retinal reference colors on the color checker device comprise at least a first set of colors representative of variations in pigmentation in the human retina and a second set of colors representative of retinal disease signs and symptoms in the human retina.

17. The method of claim 16, wherein the variations in pigmentation are based on age, ethnicity, or disease factors.

18. The method of claim 15, wherein the one or more anchor colors on the color checker device are representative of reference colors standard to the fundus imaging camera.

19. A fundus imaging system comprising:
a fundus imaging camera; and
a computing device comprising a processor and a memory, the memory having stored thereon a color characterization profile of a fundus imaging camera generated using an image of a model eye having a color checker device inserted therein, wherein the color checker device comprises a substrate configured to be inserted into the model eye and to conform to a surface curvature of the model eye when inserted therein and a color test target located on the substrate, wherein the color test target comprises a plurality of color sections configured for generating the color characterization profile of the fundus imaging camera, wherein the processor is configured to:
receive an image of a human retina captured by the fundus imaging camera; and
apply the color characterization profile to the received image to remove color bias of the fundus imaging camera.

* * * * *